United States Patent [19]

Jain et al.

[11] Patent Number: 5,716,609

[45] Date of Patent: Feb. 10, 1998

[54] THERAPEUTIC ANTI-INFLAMMATORY AND ANALGESIC COMPOSITION CONTAINING NIMESULIDE FOR USE TRANSDERMALLY AND A PROCESS FOR THE MANUFACTURE THEREOF

[75] Inventors: Rajesh Jain; Amarjit Singh, both of New Delhi, India

[73] Assignee: Panacea Biotec Limited, New Delhi, India

[21] Appl. No.: 662,477

[22] Filed: Jun. 13, 1996

[30] Foreign Application Priority Data

| Jul. 25, 1995 | [IN] | India | 1389/DEL/95 |
| Nov. 8, 1995 | [IN] | India | 2046/DEL/95 |
| Nov. 8, 1995 | [IN] | India | 2047/DEL/95 |
| Nov. 8, 1995 | [IN] | India | 2048/DEL/95 |

[51] Int. Cl.$^6$ .................. A61K 31/04; A61K 9/08
[52] U.S. Cl. .................. 424/78.05; 424/449
[58] Field of Search .................. 424/449, 78.05

[56] References Cited

U.S. PATENT DOCUMENTS

| 4,557,934 | 12/1985 | Cooper | 424/449 |
| 5,283,261 | 2/1994 | Drago | 514/604 |
| 5,380,761 | 1/1995 | Szabo et al. | 424/449 |
| 5,446,070 | 8/1995 | Mantelle | 514/772.6 |

FOREIGN PATENT DOCUMENTS

| 0159168 | 10/1985 | European Pat. Off. | 424/449 |
| 9117774 | 11/1991 | WIPO | A61K 47/48 |
| 9428031 | 12/1994 | WIPO | C08B 37/16 |
| 9534533 | 12/1995 | WIPO | C07C 311/08 |

OTHER PUBLICATIONS

Drugs 46 (Suppl 1) 1993, Nimesulide Tolerability in Osteoarthritis, Dreiser, et al. pp. 270–274.

Drugs 46 (Suppl 1) 1993, "A Multicentre Double–Blind Investigation Comparing Nimsulde and Naproxen in the Treatment of Minor Sports Injuries", A. Calligaris, et al., pp. 187–190.

Drugs 46 (Suppl 1) 1993, "The Effect of Nimesulide on Prostanoid Formation", E Magni, pp. 10–14.

Chien Yw, Novel Drug Delivery Systems, Mariel Dekker, New York, 1982, pp. 361–375.

*Primary Examiner*—Peter F. Kulkosky
*Attorney, Agent, or Firm*—Ladas & Parry

[57] ABSTRACT

Therapeutic anti-inflammatory and analgesic pharmaceutical compositions containing nimesulide for use transdermally. The pharmaceutical compositions comprise nimesulide, one or more percutaneous enhancers, one or more gelling agent/thickening agents, one or more vehicles/bases and water. The compositions may also contain one or more surfactants and a neutralizing/pH adjusting agent.

23 Claims, No Drawings

THERAPEUTIC ANTI-INFLAMMATORY AND ANALGESIC COMPOSITION CONTAINING NIMESULIDE FOR USE TRANSDERMALLY AND A PROCESS FOR THE MANUFACTURE THEREOF

TECHNICAL FIELD

This invention relates to novel therapeutic anti-inflammatory and analgesic pharmaceutical compositions containing Nimesulide which is N-(4 nitro, 2 phenoxyphenyl methane sulphonamide) for use transdermally and a process for the manufacture thereof.

BACKGROUND OF THE INVENTION

For a drug to be absorbed transdermally, it has to travel through various layers of the skin before reaching the site of action.

The layers of the skin are different in nature-some are hydrophilic while some are lipophilic (Montagna W. Parrakhal PF: The structure and Function of the skin , 3rd ed. Academic press, New York, 1974). Accordingly, any drug which is used transdermally must possess both hydrophilic and lipophillic properties. Nimesulide which is N-(4 nitro, 2 phenoxyphenyl methane sulphonamide) compound, is a highly hydrophobic drug and consequently it is considered a poor candidate for transdermal absorption. When applied to the skin, it is absorbed in very minute quantities or not absorbed at all.

A transdermal route for administration of anti-inflammatory agents offers various advantages over the oral route such as lower dosage, less toxicity/side effects, no G I irritation, no dose dumping in the body and it is more site specific (Chien YW: Novel Drug Delivery System, Marcel Dekker, New York, 1982).

The Literature and the market surveys show that at present, there exists no properly effective percutaneous formulations of Nimesulide.

In the patent for Nimesulide drug molecule (U.S. Pat. No. 3,840,597) the use of Nimesulide as an anti-inflammatory agent in the dose range of 1 mg to 500 mg per kg. body weight in the form of cream, gel, tapes and the like has been described. According to our studies, it was observed that the drug either precipitated out in the conventional formulation or precipitated on application to human skin when applied as a conventional gel or cream in the above stated dosage and practically no percutaneous absorption occurred. An overriding difficulty is the inherent insolubility of the Nimesulide in aqueous media and hence the provision of a dosage form which can contain Nimesulide in sufficiently high concentration to permit convenient use and yet meet the required criteria in terms of bioavailability e.g. enabling effective absorption from the skin.

U.S. Pat. No. 5,446,070 granted to Mantell et al. discloses a flexible, finite, bioadhesive composition. The present invention however, is not a finite composition or bioadhesive composition. The present invention comprises a composition which is non-finite in other words capable of being applied to large body areas for action at site of inflammation for instance the synovial fluids in joints.

Secondly, where the Mantell patent is restricted to a solvent range of 5 to 70 wt %, the solvent concentration of the present invention is up to 99.99% since the composition of the invention is a spreading non-finite composition.

Besides, unlike the Mantell et al Patent which requires a plasticizer, a plasticizer is not required in the present invention because of its non utility.

As regards the presence of polysaccharide, the present invention uses it along with a non polysaccharide and the usage of a polysaccharide is at a much lower % by weight than the 20% to 50% by weight as disclosed by Mantell.

Besides the polysaccharide used by Mantell in large quantities is necessary for bioadhesion which is not required in our case.

Also Mantell discloses water as an non-entity whereas in the present invention water is required in the composition.

The use of Nimesulide through intra-muscular administration as an analgesic agent has not been successful because Nimesulide is practically insoluble in water and its formulations in conventional oily bases or as suspensions result in depot formation in the muscular tissues which defies the main objective of quick relief.

The market and literature survey shows that no parenteral dosage form of Nimesulide is reported. (Drugs 48 (3) 431–454, 1994)

It is an object of the present invention to provide a therapeutic composition containing Nimesulide in combination with other compounds which alter the hydrophobic property of Nimesulide, and a process for the manufacture thereof thus making it possible for the composition to be used for direct application on the skin for the treatment of inflammation through transdermal absorption.

It is a further object of the present invention to provide a novel therapeutic composition containing Nimesulide in combination with other compounds which alter the physico-chemical property of Nimesulide, thus making it possible for the composition to be used for direct application on the skin for the treatment of inflammation through transdermal absorption, at dose levels much lower than the dose levels according to the known art.

SUMMARY OF THE INVENTION

The present invention provides a Novel Therapeutic Anti-inflammatory and Analgesic pharmaceutical composition for topical use which comprises:

1. Nimesulide: 0.1% to 10% w/w
2. Percutaneous absorption: 90% to 99.9% w/w enhancing vehicle base The said Percutaneous enhancing vehicle base acts as a microcarrier preconcentrate or a microcarrier and comprises:

1. Percutaneous enhancer: 0.5% to 60% w/w as herein described
2. Surfactant as herein: 0.0% to 12% w/w described
3. Gelling agent/Thickening: 0.2% to 19% w/w agent as herein described
4. One or more vehicle/base: 5% to 97% w/w. including water as herein described Preferably the percutaneous enhancing base comprises:

1. Percutaneous enhancer: 6% to 15% w/w. as herein described.
2. Surfactant as herein: 0.5% to 12% w/w described
3. Gelling agent/Thickening: 0.5% to 19% w/w agent as herein described
4. One or more vehicle/base: 5% to 60% w/w. including water as herein described One or more percutaneous enhancers can be used in compositions according to this invention. One or more surfactants can be used in compositions according to this invention. One or more gelling agents/thickening agents can be used in compositions according to this invention.

Water is required for the composition in the range of 1% to 15% w/w, preferably 9% to 11% w/w and more preferably in the range of 9.5% to 10.5% w/w.

Besides the above disclosed ingredients the composition for topical use also comprises a neutralizing agent/pH adjusting agent such as herein described in the range of 0.0% to 2.0%.

DETAILED DESCRIPTION OF THE INVENTION

According to the present invention, it has been found that it is possible to solubilize and deliver a highly hydrophobic drug like Nimesulide to the site of action through a transdermal route. The present invention involves the process of incorporation of Nimesulide in a formulation which can solubilize the drug and transport the drug through the skin barriers, in intact condition to the site of action.

Preferably the percutaneous enhancing base comprises:
1. Percutaneous enhancer: 6% to 15% w/w. as herein described.
2. Surfactant as herein: 0.5% to 12% w/w described
3. Gelling agent/Thickening: 0.5% to 19% w/w agent as herein described
4. One or more vehicle/base: 5% to 60% w/w. including water as herein described Preferably nimesulide is in the range of 1% to 5% w/w.

More preferably the composition for topical use also comprises a Neutralising agent/ph adjusting agent as herein described in the range of 0.0% to 2.0%.

The novel Therapeutic Anti-Inflammatory and Analgesic Composition for topical use according to the present invention, is prepared by the process which comprises the following steps:

(a) 0.5% to 30% w/w of a Percutaneous enhancer, as herein described, is mixed with 2.5% to 30% w/w of one or more Vehicle or base, as herein described, in a container by stirring and to the mixture obtained 0.1% to 10% w/w of Nimesulide is added and stirred till completely dissolved.

(b) 0.5% to 12% w/w of a Surfactant, as herein described, 0.2% to 50% w/w of a Gelling agent/thickening agent, as herein described, and 2.5% to 30% w/w of one or more Vehicle/Base, as herein described, are mixed in a homogeniser to obtain a homogenised mixture.

(c) The mixture obtained in step (a) is added to the homogenised mixture obtained in step (b) under stirring without vortex formation to avoid aeration. The mixture is neutralised or its pH adjusted by addition of 0.0% to 2.0% of a neutralizing agent or a pH adjusting agent to bring the pH of the product on the acidic side, as herein described, with slow stirring resulting in the preparation of the desired Anti-inflammatory and Analgesic Composition.

As Percutaneous enhancer any known Percutaneous enhancer may be used preferably a $C_{12-24}$ mono or poly-unsaturated fatty acids such as vaccenic, cis-vaccenic, Linoleic, Linolenic, elaidic, oleic, petroselinic, erucic or nervonic acid or any of their corresponding alcohols, especially oleic acid or oleyl alcohol or 1-dodecylazacycloheptane-2-one also known as azone; sulphoxides like dimethylsuphoxide, n-decyl methylsulphoxide; Amides like dimethylacetamide, dimethylformamide and N, N-diethylm-toluamide; Pyrrolidones like 2-pyrrolidone and N-methyl-2 Pyrrolidone.

As surfactant, any pharmaceutically acceptable hydrophilic or lipophilic surfactant or mixture thereof may be used, especially suitable for this purpose are the reaction products of natural or hydrogenated vegetable oils and ethylene glycol i.e. polyoxyethylene glycolated natural or hydrogenated vegetable oils, e.g. polyoxyethylene glycolated natural or hydrogenated castor oils; especially various tensides available under the trade name CREMOPHOR particularly CREMOPHOR RH 40 and CREMOPHOREL. Also suitable for use are the various surfactants available under the trade name NIKKOL e.g NIKKOL HCO-60.

Polyoxyethlene-Sorbitan fatty acid esters e.g. mono and trilauryl, palmityl, stearyl and oleyl esters e.g. those available under the trade name TWEEN preferably TWEEN 40 and TWEEN 80.

Polyoxyethylene-polyoxypropylene block copolymers e.g. especially those available under the trade name POLOXAMER preferably POLOXAMER 188.

Polyoxyethylene fatty acid esters, for example polyoxyethylene stearic acid esters, commercially available under the trade name MYRJ as well as polyoxyethylene fatty acid esters commercially available under the trade name CEπOL HE;

Propylene glycol mono-and di-fatty acid esters such as propylene glycol dicaprylate, propylene glycol dilaurate, propylene glycol hydroxysterate, propylene glycol isostearate, propylene glycol laurate, propylene glycol ricinoleate, propylene glycol stearate;

Examples of suitable lipophilic surfactants include trans-esterification products of natural vegetable oil triglycerides and polyalkylene polyols. Preferred are products obtained by trans-estrification of 2 molar parts of natural vegetable oil triglycerides with one molar part of polyethylene glycol (e.g. having an average molecular weight of from 200 to 800). Various forms of such trans-estrification product are commercially available under the trade name LABRAFIL, preferably LABRAFIL M 1944 CS;

Sorbitan fatty acid esters commercially available under the trade name SPAN including Sorbitan monolauryl, monopalmityl, -monostearyl, -tristearyl.-monooleyl and -trioleyl esters;

Monoglycerides e.g. Glycerol monooleate, glycerol monopalmitate and glycerol monostearate commercially available under the trade names MYVATEX, MYVAPIEX and MYVEROL.

As Gelling Agent/Thickening agent, any known such pharmaceutically acceptable agent may be used including synthetic or semi-synthetic polymeric materials, polyacrylate and polyacrylate co-polymeric resins e.g. polyacrylic acid and polyacrylic acid/methacrylic acid resins, commercially available under the trade name CARBOPOL, particularly CARBOPOL 934, 940 and 941 and EUDRAGIT, particularly EUDRAGIT E, L, S, RL, and RS;

Cellulose and cellulose derivatives including alkyl celluloses e.g. methyl-, ethyl-, and propyl-celluloses; hydroxyalkyl-celluloses e.g. hydroxypropyl cellulose, hydroxypropyl alkylcellulose such as hydroxypropylmethyl- cellulose, acylated celluloses e.g. cellulose-acetates, cellulose acetate phthalates and salts thereof such as sodium carboxymethyl cellulose;

Polyvinyl resins including polyvinylacetates and alcohols as well as other polymeric materials including alginates e.g alginic acid and salts thereof e.g. sodium alginate and propylene glycol alginate.

As Neutralising/pH adjusting agent any such conventional such agent may be used including sodium bicarbonate, sodium hydroxide, potassium hydroxide, borax, disodium hydrogen phosphate and sodium dihydrogen phosphate. Preferably polar organic amines like diethylamine, diisopropanolamine, triethylamine and triethanolamine may be used.

As vehicles/base, the following may be used:

Pharmaceutically acceptably lower (having $C_{1-5}$) alkanols, particularly ethanol; water soluble macrogels like polyethylene glycol having an average molecular weight from 200 to 600: 1,2-propylene carbonate, propane-1, 2-diol and 1,2,-propylene glycol; glycerol triacetate or (1,2,3,)-triacetin; lower ketones, particularly acetone and 1,2,3-propanetriol may be incorporated.

Water in varying concentration may be added to provide the requisite hydrophilic nature to the composition.

Pharmaceutically acceptable $C_{1-5}$ alkyl or tetra hydrofurfuryl; di or partial ether of a low molecular weight mono or polyoxy-alkanediol particularly those available under the trade names TRANSCUTOL and COLYCOFUROL.

As the base having lipophilic phase for the preparation of emulsions, fatty acid triglycerides, preferably medium chain fatty acid triglycerides; vegetable oils like coconut oils, olive oil, castor oil and their derivatives; and ethyl oleate may be used.

As base, for the preparation of the said therapeutic composition in the form of an ointment, fatty acids, fats, oils and waxes of animal origin like bees wax, spermacetii, wool fat, waxes of vegetable origin or mineral origin like hard, soft and liquid paraffin may be used.

The topical dosage forms are formulated suitably such that the resultant product is easy to apply and is non-staining.

For the therapeutic composition in the form of an aerosol formulation for topical applications, pharmaceutically acceptable propellants may be used such as chlorofluoro carbons e.g. the Propellant 11, Propellant 12, Propellant 114; Hydrocarbon propellants like n-butane, isobutane and propane; compressed gas propellants e.g. Nitrous oxide, carbon dioxide, and nitrogen.

The novel therapeutic composition according to the present invention may be used in the following forms:

1. Topical aqueous gel.
2. Oil-in-water or water-in-oil emulsion or microemulsion or cream.
3. Solution for topical applications.
4. Ointment.
5. Aerosol formulation for topical applications.

The therapeutic composition according to the present invention may be applied on the skin by utilising a physical form of energy like electrical energy or ultrasonic energy to effect better percutaneous absorption of the drug.

The invention will now be described with reference to the foregoing examples:

EXAMPLE 1

Preparation of topical gel dosage form

| Sl. No. | Component | Quantity |
|---|---|---|
| 1. | Nimesulide | 2.0 g |
| 2. | Dimethylacetamide | 22.0 g |
| 3. | Ethyl Alcohol | 40.0 g |
| 4. | Acetone | 10.0 g |
| 5. | Cremophor RH 40 | 4.0 g |
| 6. | Propylene glycol | 38.0 g |
| 7. | Polyethylene glycol 400 | 48.8 g |
| 8. | Carbopol 934 | 4.0 g |
| 9. | Water | 30.0 g |
| 10. | Diethylamine | 1.2 g |
| | Total | 200.0 g |

Step (a) Dimethylacetamide is mixed with ethyl alcohol and acetone at 30° C. in a container with stirring. To the mixture obtained Nimesulide is added and stirred till completely dissolved.

Step (b) Propylene glycol, polyethylene glycol 400 and water are mixed in homogenizer. To the homogenised mixture obtained, 1.5% w/w of carbopol 934 is added in small amounts at a time at room temperature and the speed of the homogenizer is kept at approximately 1500–2000 rpm.

Step (c) The mixture obtained in step (a) is added to the mixture obtained in step (b) under stirring without vortex formation to avoid aeration preferably under vacuum (25 mm of Hg). The mixture obtained is neutralised by slow addition of Diethylamine with slow stirring at a temperature of 25°–30° C. and under vacuum (25 mm of Hg) to affect gel formation.

EXAMPLE 2

Preparation of emulsion type topical dosage form.

| Sl. No. | Component | Quantity |
|---|---|---|
| 1. | Nimesulide | 1.0 g |
| 2. | Transcutol | 35.0 g |
| 3. | Water | 10.0 g |
| 4. | Disodium hydrogen phosphate | 0.1 g |
| 5. | Cremophor RH 40 | 5.0 g |
| 6. | Labrafil M 1944 CS | 10.0 g |
| 7. | Glyceryl monostearate | 8.0 g |
| 8. | Stearic acid | 13.0 g |
| 9. | Ethyl oleate | 2.9 g |
| 10. | Dimethyl sulphoxide | 15.0 g |
| | Total | 100.0 g |

Dissolve Nimesulide in a mixture of (6), (7), (8), (9) and (10) with warming. Separately mix (2), (3), (4) and 5 and slowly add the Nimesulide mixture to it with stirring.

EXAMPLE 3

Preparation of a solution type dosage form for topical application.

| Sl. No. | Component | Quantity |
|---|---|---|
| 1. | Nimesulide | 1.0 g |
| 2. | Dimethyl formamide | 10.0 g |
| 3. | Poloxamer 188 | 2.0 g |
| 4. | Ethyl alcohol | 20.0 g |
| 5. | Propylene glycol | 25.0 g |
| 6. | Polyethylene glycol 400 | 42.0 g |
| 7. | Hydroxypropylmethyl-cellulose | 1.0 g |
| 8. | Triethanolamine | 0.2 g |
| 9. | Water | 1.0 g |
| | Total | 100.0 g |

Nimesulide is dissolved in (2) with stirring and (3), (4), (5), (6), (7) and (8) are added to obtain a clear solution with stirring.

EXAMPLE 4

Preparation of ointment type dosage form topical application.

| Sl. No. | Component | Quantity |
| --- | --- | --- |
| 1. | Nimesulide | 2.0 g |
| 2. | Dimethylsulphoxide | 21.0 g |
| 3. | Glycerylmonostearate | 16.0 g |
| 4. | Mineral oil | 62.0 g |
| 5. | White petrolatum | 97.0 g |
| 6. | Water | 2.0 g |
|   | Total | 200.0 g |

Warm (3), (4) and (5) and add with stirring a solution of Nimesulide in dimethyl sulphoxide.

EXAMPLE 5

Preparation of an aerosol dosage form for topical use.

| Sl. No. | Component | Quantity |
| --- | --- | --- |
| 1. | Nimesulide | 1.0 g |
| 2. | Dimethylacetamide | 10.0 g |
| 3. | Ethyl alcohol | 10.0 g |
| 4. | Cremophor RH 40 | 10.0 g |
| 5. | Propellant 114 | 29.0 g |
| 6. | Propellant 12 | 39.0 g |
| 7. | Water | 1.0 g |
|   | Total | 100.0 g |

The analgesic activity of the therapeutic composition, prepared according to the present invention, was found to be dose dependent and passed the tests of subacute toxicity and undue toxicity.

The dose levels of the novel Anti-inflammatory and Analgesic composition, according to the present invention, are comparatively much lower than the dose levels of the Conventional Nimesulide formulations for equally effective results.

The various forms of the therapeutic composition prepared according to the present invention were subjected to in-vitro drug release studies using modified USP dissolution apparatus attached with enhancer cell (Pharm Tech. Jan. 1995, 52–58). The dissolution media used was phosphate buffer pH 7.4. The results indicated that the cumulative drug release and permeation flux were proportional to the drug load.

The compositions were also subjected to standard pharmacological test methods to measure anti-inflammatory activity such as rat paw oedema and quinea pig erythema. These tests showed significant activity when compared to placebo.

The therapeutic compositions were also tested on sixty healthy human volunteers for irritation or other undue side effects. No incidence of irritation/side effects was reported.

Since many apparently different embodiments of the present invention could be made without departing from the spirit and scope thereof, it is intended that the description of the invention herein be interpreted as being illustrative only and not limiting in any manner whatsoever.

We claim:

1. A therapeutic anti-inflammatory and analgesic pharmaceutical composition for topical/transdermal use containing a substantial amount of water to render it more absorbable and water soluble which comprises:

nimesulide from 0.1% to 10% w/w and percutaneous absorption enhancing vehicle/base from 90% to 99.9% w/w wherein said percutaneous absorption enhancing vehicle base comprises:

percutaneous enhancer from .0.5% to 60% w/w and vehicle/base from 5.0% to 97% wherein said vehicle/base includes water in an amount from 1% to 15% w/w.

2. The composition as claimed in claim 1 further comprising 0.2% to 19% w/w of the gelling agent/thickening agent.

3. The composition of claim 1 further comprising up to 12% w/w of a surfactant.

4. The composition as claimed in claim 1 further comprising a neutralizing agent/pH adjusting agent in an amount up to 2.0% w/w.

5. The composition as claimed in claim 1 wherein the percutaneous enhancer is selected from $C_{12-24}$ mono or poly-unsaturated fatty acids or any of their corresponding alcohols.

6. The composition as claimed in claim 1 wherein the percutaneous enhancer is selected from sulphoxides, amides or pyrrolidones.

7. The composition as claimed in claim 6 wherein the percutaneous enhancer is dimethylacetamide.

8. The composition as claimed in claim 3 wherein the surfactant is a pharmaceutically acceptable hydrophilic or lipophilic surfactant or mixture thereof.

9. The composition as claimed in claim 8 wherein the surfactant is selected from polyoxyethylene-sorbitan fatty acid esters, polyoxyethylene-polyoxyproylene block copolymers, polyoxyethylene fatty acids esters, propylene glycol mono- and di-fatty acid esters, lipophilic surfactants, sorbitan fatty acid esters, or monoglycerides.

10. The composition as claimed in claim 2 wherein said gelling/thickening agent is selected from synthetic or semi-synthetic polymeric materials, polyacrylate and polyacrylate co-polymeric resins, cellulose and cellulose derivatives or polyvinyl resins.

11. The composition as claimed in claim 1 wherein water is present in the range of 9% to 11% w/w.

12. The composition as claimed in claim 11 wherein water is present in the range of 9.5% to 10.5% w/w.

13. The composition as claimed in claim 4 wherein the neutralizing/pH adjusting agent is selected from the group comprising sodium bicarbonate, sodium hydroxide, potassium hydroxide, borax, disodium hydrogen phosphate, and sodium dihydrogen phosphate.

14. The composition as claimed in claim 4 wherein neutralizing/pH adjusting agent is a polar organic amine.

15. The composition according to claim 1 wherein the vehicle/base is selected from pharmaceutically acceptably lower ($C_{1-5}$) alkanols; water soluble macrogols; 1,2-propylene carbonate; propane-1, 2-diol; 1,2-propylene glycol; glycerol triacetate; glycerol (1,2,3)-triacetin or lower ketones.

16. A therapeutic anti-inflammatory and analgesic pharmaceutical composition for topical transdermal use which comprises:

nimesulide: 0.1% to 10% w/w, percutaneous enhancer: 0.5% to 60% w/w, gelling agent/thickening agent: 0.2 to 19% w/w, vehicle/base including water: 5% to 97% w/w and up to 12% w/w of surfactant.

17. A therapeutic anti-inflammatory and analgesic pharmaceutical composition for topical transdermal use which comprises:

nimesulide: 0.1% to 10% w/w,
percutaneous enhancer: 0.5% to 60% w/w,
gelling agent/thickening agent: 0.2% to 19% w/w,
vehicle/base: 5% to 97% w/w
up to 12% w/w of surfactant, and up to 2% w/w of neutralizing/pH adjusting agent.

18. A process for the production of a therapeutic anti-inflammatory and analgesic pharmaceutical composition for topical/transdermal use which comprises:
   a) mixing 0.5% w/w to 30% w/w of a percutaneous enhancer with 2.5% to 30% w/w of one or more vehicles or bases;
   b) adding to the mixture of step a) 0.1% w/w to 10% w/w of nimesulide followed by stirring the mixture until completely dissolved:
   c) mixing separately 0.5% w/w to 12% w/w of a surfactant, 0.2% w/w to 50% w/w of a gelling agent/thickening agent and 2.5% w/w to 30% w/w of one or more vehicles or bases and mixing the entire mixture; and
   d) adding the mixture obtained in step b) to the mixture obtained in step c) under stirring to obtain the composition.

19. A process as claimed in claim 18 wherein a neutralizing agent or a pH adjusting agent is added to the composition in step d) to neutralize or adjust the pH or the mixture.

20. A process as claimed in claim 19 wherein the said neutralizing agent/pH adjusting agent is added in an amount of up to 2.0% w/w.

21. The composition according to claim 1 which is non-staining.

22. The composition according to claim 16 which is non-staining.

23. The composition according to claim 17 which is non-staining.

* * * * *